United States Patent [19]

Trizisky

[11] 4,120,660
[45] Oct. 17, 1978

[54] METHOD AND APPARATUS FOR THE DETERMINATION OF OXIDATIVE STABILITY OF POLYMERS UNDER SHEAR CONDITIONS

[75] Inventor: Joseph Donnelly Trizisky, Amherstview, Canada

[73] Assignee: E. I. Du Pont de Nemours and Company, Wilmington, Del.

[21] Appl. No.: 849,934

[22] Filed: Nov. 9, 1977

[30] Foreign Application Priority Data

Nov. 9, 1976 [CA] Canada .................................. 265588

[51] Int. Cl.² ........................................... G01N 27/00
[52] U.S. Cl. .................................... 23/230 R; 422/68; 422/83
[58] Field of Search ........................... 23/230 R, 253 R

[56] References Cited

U.S. PATENT DOCUMENTS

| 3,013,004 | 12/1961 | Koble et al. ................ 23/253 R X |
| 3,053,640 | 9/1962 | Kirkpatrick et al. .......... 23/253 R X |
| 3,550,454 | 12/1970 | Wolkober et al. ............ 23/253 R X |
| 3,764,484 | 10/1973 | Platt ........................... 23/230 R X |
| 3,868,221 | 2/1975 | Howard et al. ............... 23/230 R |

Primary Examiner—Robert M. Reese

[57] ABSTRACT

Apparatus for the determination of the oxidative stability of polymers exhibiting viscous or visco-elastic flow at the temperature of the determination is disclosed. The apparatus comprises a mixing head having means to subject polymer to shear, means to measure the oxygen content of gas, means to circulate the gas from the mixing means to the analyzing means and back to the mixing head and pressure control means to control the pressure of the gas at atmospheric pressure without extraneous dilution. In a preferred embodiment the pressure control means includes an elongated tube having a ratio of length to diameter of at least 800. A method for determining the oxidative stability of polymer under shear conditions is also disclosed. The apparatus and process may be used for the determination of the oxidative stability of, for example, elastomeric and thermoplastic polymers under conditions resembling the conditions under which such polymers are fabricated into articles.

18 Claims, 4 Drawing Figures

METHOD AND APPARATUS FOR THE DETERMINATION OF OXIDATIVE STABILITY OF POLYMERS UNDER SHEAR CONDITIONS

FIELD OF THE INVENTION

The present invention relates to the oxidation of polymer, especially molten thermoplastic polymers, and in particular to the determination of the oxidative stability of such polymers.

BACKGROUND OF THE INVENTION

Polymers, especially thermoplastic polymers, are usually manufactured in the form of pellets or powders. In order to manufacture articles from such polymers the pellets or powders are usually heated so as to convert the polymers to a viscous, especially molten, state and the resultant polymer is then fabricated into articles of the desired shape. Such fabrication of articles from thermoplastic polymers may be accomplished using, for example, extrusion, injection moulding or rotational moulding techniques.

Polymers are susceptible to oxidation. The oxidation of polymers is temperature-dependent, occurring more rapidly at elevated temperatures. Oxidation of a polymer, which may occur by a number of mechanisms depending on the particular polymer and the conditions to which the polymer is subjected, affects the properties of articles fabricated from the polymer. The amount of oxidation of a polymer during the manufacture of articles from the polymer is frequently important in determining the subsequent useful life of the article in a particular end use.

Moreover, the effects of oxidation of polymers, especially the effects resulting from oxidation during the manufacture of articles from the polymer, may not become apparent in the properties of the article for months or even years after the manufacture of the article.

In view of the importance of minimizing the amount of oxidation occurring at elevated temperatures during the manufacture of articles from a polymer, stabilizers especially those stabilizers known as antioxidants are incorporated into the polymer. The type and amount of stabilizer depends in particular on the type of polymer, the processing conditions used in the manufacture of articles and the end use for the articles. Mixtures of stabilizers are sometimes used especially if the mixture has synergistic antioxidant effects. In order, for example, to evaluate the effectiveness of a particular antioxidant in a polymer there is a need for apparatus in which the oxidation of polymers may be evaluated in a relatively short period of time.

A large number of techniques have been used in attempts to evaluate the oxidative stability of polymers and the effectiveness of antioxidants in polymers in relatively short periods of time. For example, the oxidation of polymers may be studied using oven-aging techniques in which polymer compositions, usually in the form of test samples, are maintained at elevated temperatures especially temperatures well below the melting point of the polymer. Periodic determinations of the physical and/or chemical properties of the polymer are made. Alternatively differential thermal analysis techniques may be used to study the degradation of polymers, as is described, for example, in U.S. Pat. No. 3,868,221 of J. B. Howard and R. F. Westover, which issued Feb. 15, 1975. The rate of oxygen up-take of molten polymers, especially under elevated pressures of oxygen, may be determined using manometric or volumetric techniques. The above techniques are generally characterized by the use of solid polymers or of molten polymers that are not subjected to shear conditions and by the use of samples of relatively small size. Correlations of the results obtained using such techniques and the oxidation actually occurring in the manufacture of articles using, for example, extrusion techniques may be somewhat tenuous.

The degradation of some polymers under so-called "milling" conditions may be determined according to the procedure of ASTM D-1243 or by monitoring the torque on shearing means while subjecting polymers to heat and shear.

Techniques for determining the oxidative stability of polymers and/or the effectiveness of antioxidants are discussed by W. L. Hawkins in "Polymer Stabilization" Wiley-Interscience 1972 especially pages 422–436 thereof.

In spite of the variety of techniques for monitoring the oxidation of polymers there is a need for apparatus capable of being used for determining such oxidation with greater precision and under conditions more closely resembling the condition under which polymers are fabricated into articles.

SUMMARY OF THE INVENTION

An apparatus capable of being used to determine the oxidative stability of polymers under shear conditions has now been found.

Accordingly, the present invention provides apparatus for the determination of the oxidative stability of polymers exhibiting viscous or visco-elastic flow at the temperature of said determination, said apparatus comprising
  (a) a mixing head having a cavity adapted to receive thermoplastic polymer and to be sealed;
  (b) means located within said cavity capable of subjecting polymer to shear;
  (c) heating means adapted to control the temperature of polymer in said mixing head;
  (d) analyzing means capable of measuring the oxygen content of a gas;
  (e) circulating means adapted to circulate gas from within the mixing head through the analyzing means and back to the mixing head;
  (f) pressure control means adapted to control the pressure of gas at atmospheric pressure, said pressure control means inhibiting extraneous dilution; and
  (g) means adapted to replace a first gas with a second gas.

In a preferred embodiment of the apparatus of the present invention the heating means is an electrical heating means.

In another preferred embodiment the pressure control means comprises an elongated tube, especially an elongated tube having attached at one end thereof a vessel equipped with a small opening connecting with the atmosphere, and adapted to be flushed with inert gas, the other end of said elongated tube being connected to the means to circulate the gas.

The present invention also provides a method for determining the oxidative stability of polymers under shear conditions, said method comprising the steps of:
  (a) heating polymer to a pre-selected temperature in the presence of a first gas that is inert with respect to the polymer, said polymer being viscous or visco-elastic at the pre-selected temperature;

(b) replacing the inert gas with an oxygen-containing gas, said oxygen-containing gas being at atmospheric pressure; and (c) while subjecting the polymer to shear measuring the amount of oxygen in the oxygen-containing gas over a period of time, the pressure of the oxygen-containing gas being maintained at atmospheric pressure by addition of a second gas that is inert with respect to the polymer.

DESCRIPTION OF THE DRAWINGS

The present invention will generally be described hereinafter with reference to the embodiments shown in the drawings in which.

DESCRIPTION OF THE INVENTION

Figure 1:
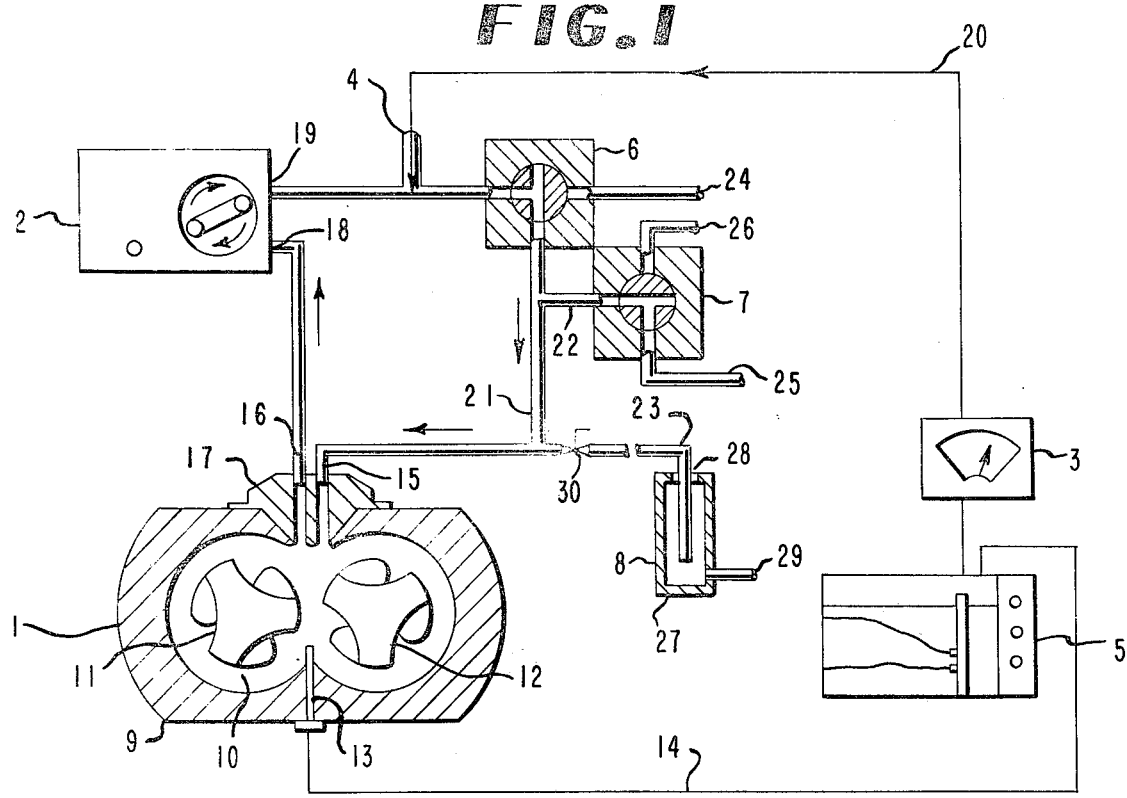
FIG. 1 is a schematic representation, partially in section, of an apparatus of the present invention.

In the embodiment illustrated by FIG. 1 the apparatus of the present invention comprises a mixing head 1, a pump 2, an oxygen analyzer 3 having a sensor 4, and a recorder 5, valves 6 and 7 and vent 8. Mixing head 1 is comprised of a metal block 9 having a cavity 10 therein. Cavity 10 is adapted to contain polymer (not shown) on which the determination of the oxidative stability is to be carried out. Block 9 has means (not shown) for removal of polymer especially after the determination of oxidative stability has been carried out. Rotors 11 and 12 are located within cavity 10. Rotors 11 and 12 are adapted to subject polymer in cavity 10 to shear and are rotatable in a controlled manner by means of shafts (not shown) attached to each of rotors 11 and 12. Cavity 10 is of a shape adapted to contain rotors 11 and 12 and the polymer. The volume of cavity 10 will depend on the size of the sample of polymer on which it is desired to carry out the determination of oxidative stability, suitable volumes being for example, 20-100 cm$^3$ and especially 30-70 cm$^3$. A thermocouple 13, preferably a dual thermocouple, passes through metal block 9 and extends into cavity 10; thermocouple 13 being centrally located with respect to the cross-section of cavity 10. Thermocouple 13 is connected by electrical connection 14 to recorder 5 and is used in the control of the temperature of polymer in cavity 10. Metal block 9 is adapted to be heated by heating means that are not shown. Cavity 10 is in fluid flow communication with inlet pipe 15 and outlet pipe 16, both of which pass through removable plug 17 (shown in greater detail in FIG. 2), which is centrally located and in the upper portion of block 9.

Outlet pipe 16 is connected to inlet 18 of pump 2 which in the embodiment shown is a peristaltic pump. Outlet 19 of pump 2 is connected to sensor 4 of oxygen analyzer 3, sensor 4 being connected to oxygen analyzer 3 by electrical connection 20. Oxygen analyzer 3 is connected to recorder 5.

Sensor 4 is connected in turn with inlet pipe 15 of mixing head 1 by means of a pipe generally indicated by 21. Valve 6 is located in pipe 21. Pipe 21 is also connected to valve 7 and to vent 8 by means of connecting pipe 22 and elongated vent pipe 23 respectively. Valve 6 is a three-way valve and is connected to a source of vacuum (not shown) by means of vacuum pipe 24. Valve 7 is also a three-way valve, being connected to a supply (not shown) of an oxygen-containing gas by means of pipe 25 and to a supply (not shown) of inert gas, for example nitrogen, by means of pipe 26.

Vent 8 is comprised of a vessel 27 having an orifice 28 at one end and an inlet 29 at the other end. Inlet 29 is connected to a source (not shown) of inert gas, for example nitrogen. Elongated vent pipe 23 extends through orifice 28 and partially into vessel 27. Valve 30 is located in elongated vent pipe 23 between pipe 21 and vessel 27. Elongated pipe 23 may be replaced at least in part by sensitive electronic means for the control of pressure.

The ratio of length to diameter (L/D) of the elongated vent pipe 23 will depend in part on the type of rotors, volume of the apparatus and type of pump used. It is preferable to use an elongated vent pipe 23 having an L/D of at least 600 and in particular of at least 800 in order to effectively inhibit extraneous dilution of oxygen-containing gas in the apparatus.

Figure 2:
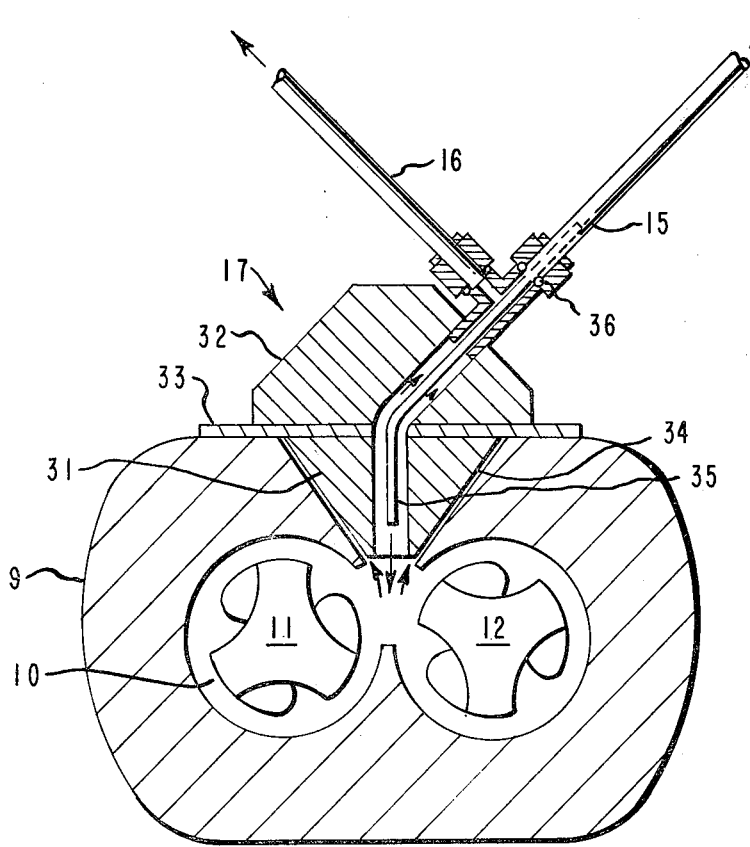
FIG. 2 is a schematic representation, in section, of a mixing head of apparatus of the present invention.

Removable plug 17 is shown in greater detail in FIG. 2. Removable plug 17 is comprised of three parts, viz, lower section 31, upper section 32 and seal 33. Lower section 31 of removable plug 17 has the same shape, that of a truncated wedge in the embodiment shown, as orifice 34. Orifice 34 is centrally located in the upper portion of block 9 and is in fluid-flow communication with cavity 10 of block 9. Lower section 31 of removable plug 17 fits into orifice 34 so as to form a flush fit with the outside of block 9. Seal 33 of removable plug 17 extends over and beyond lower section 31 so as to form a seal against block 9. Upper section 32 abuts seal 33. Elongated cavity 35 extends through upper section 32, seal 33 and lower section 31 and forms fluid-flow communication between cavity 10 of block 9 and the exterior of upper section 32 of removable plug 17. Inlet 15 extends through elongated cavity 35. The remainder of elongated cavity 35 forms outlet 16. Exterior to upper section 32, outlet 16 branches away from inlet 15, seals for example seal 36 being provided so as to accomplish the branching of inlet 15 and outlet 16.

Figure 3:
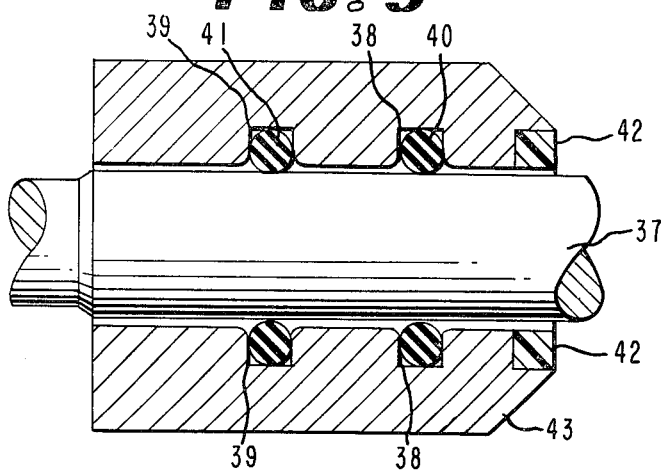
FIG. 3 is a schematic representation, in section, of the seal on the shaft of the rotors of the mixing head.

The sealing of the shaft 37 of each of rotors 11 and 12 in cavity 10 is shown in FIG. 3. Shaft 37 extends through a bushing 43, especially an OILITE bushing, which is adapted for an interference fit into block 9 (not shown). Bushing 43 has two circular grooves 38 and 39 juxtaposed to shaft 37. O-rings 40 and 41 are in circular grooves 38 and 39. O-rings 40 and 41 are in sliding engagement with shaft 37 and are in contact with the walls of grooves 38 and 39. O-rings 40 and 41 are of an external diameter slightly greater than the external diameter of grooves 38 and 39 so as to form an effective seal by peripheral compression, as is known in for example ROTOSEAL seals. Seal 42, which may be for example fabricated of TEFLON fluorocarbon polymer, is in sliding engagement with shaft 37 and is adapted to prevent the flow of polymer in cavity 10 (not shown) along shaft 27.

In operation polymer is placed in cavity 10 by means of orifice 34, the temperature of block 9 normally being substantially that at which the determination is to be carried out. Removable plug 17 is then placed in orifice 34 and clamped by means (not shown). Air in the apparatus is replaced by nitrogen by closing valves 7 and 30, connecting valve 6 to pipe 24, applying a vacuum to pipe 24 and then supplying nitrogen through pipe 26. Valves 7 and 30 are closed during the evacuation procedure. The polymer is then heated in an atmosphere of nitrogen to the desired temperature. The apparatus is evacuated again, using the procedure described above, and an oxygen-containing gas, for example, air is admitted through pipe 25. Pump 2 is immediately started and valve 30 is opened. Oxygen analyzer 3 records the oxygen content of the gas in the apparatus. Throughout the determination nitrogen is passed slowly through inlet 29 into vessel 27 and out through orifice 28. As the oxygen content of the gas in the apparatus decreases nitrogen enters through pipe 23, thereby maintaining the pressure of the gas in the apparatus at atmospheric pressure and essentially eliminating any tendency of atmospheric air to leak into the apparatus during the determination. The polymer is subjected to shear using rotors 11 and 12 thereby shearing and effectively mixing the polymer, such mixing being so that the oxidation of the polymer is homogeneous and not dependent on diffusion of oxygen.

While the use of nitrogen described above is preferred, the nitrogen may be replaced in whole or in part with a gas that is inert with respect to the polymer under the conditions of the determination of oxidative stability. The preferred oxygen-containing gas is air.

Figure 4:
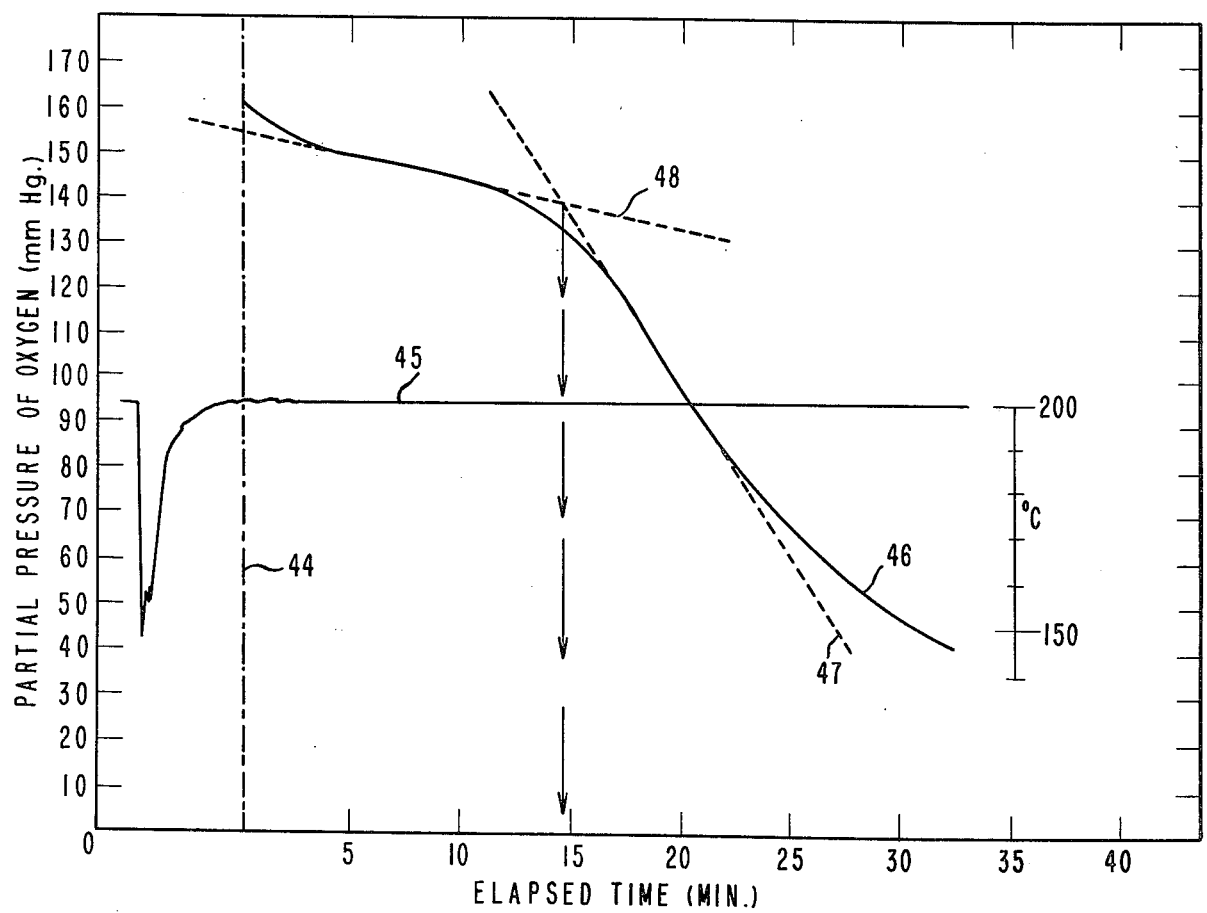
FIG. 4 is a representation of results obtained using the apparatus of the present invention.

The results of an experiment for the determination of the rate of oxidation of a homopolymer of ethylene are illustrated by FIG. 4. FIG. 4 is a representation of the results as recorded on recorder 5 and is in graphical form. One axis of the graph indicates the time elapsed as measured from the introduction of air to the heated polymer. The other axis of the graph indicates (a) the temperature in degrees Celsius of the molten polymer, as measured by thermocouple 13 and (b) the partial pressure of oxygen in the gas in contact with the polymer, as measured by oxygen analyzer 3, in mm of mercury.

Line 44 indicates the beginning of the experiment, i.e., a time of zero minutes. Line 45 indicates that the temperature of the polymer has stabilized to within ± 1° C. of the desired polymer temperature of 200° C. prior to commencement of the experiment. Line 46 indicates the partial pressure of oxygen in the gas in contact with the polymer. After an initial relatively rapid decrease in partial pressure of oxygen, the rate of decrease of partial pressure is constant for a period of time. Subsequently the rate of decrease of partial pressure increases and then reaches a second, and higher, rate of decrease of oxygen partial pressure. Line 47 drawn through the second steady rate of decrease of partial pressure is a measure of the rate of oxidation of the polymer. The intersection of line 48, drawn through the first steady rate of decrease of partial pressure, and line 47 is a measure of the so-called induction period, which is measured from line 44, in the oxidation of the polymer. Line 48 is a measure of the rate of oxidation of the polymer during the induction period.

The polymers on which oxidative stability may be determined using the present invention are viscous or visco-elastic under the conditions at which the determination is made. While determinations are usually made at elevated temperatures, for example temperatures similar to those used in the fabrication of articles, e.g., by extrusion, injection moulding, rotational moulding, thermoforming techniques, the present invention is capable of being used for determinations of oxidative stability of some polymers at about ambient temperatures. Examples of polymers on which determinations of oxidative stability may be made are thermoplastic polymers, e.g., poly-α-olefins, especially homopolymers of ethylene, copolymers of ethylene and higher α-olefins and polypropylene, polyamides and polyesters, and elastomeric polymers, e.g., ethylene/propylene copolymers, ethylene/propylene/diene copolymers and diene rubbers, and mixtures thereof. The polymers may contain antioxidents and other stabilizers, fillers, pigments and the like.

The apparatus of the present invention is capable of being used for the determination of the oxidative stability of polymers under a variety of conditions and to obtain a variety of information on the oxidation of polymers and/or the effectiveness of antioxidants. For example, the apparatus may be used to determine the effect of temperature on the rate of oxidation of a particular polymer/antioxidant composition. Alternatively the apparatus may be used for the testing of a variety of polymer/antioxidant compositions especially in which the amount and/or type of antioxidant is varied or for measurements of the effect of physical and/or chemical properties of polymers or compositions thereof. Such determinations may involve only the measurement of the induction period or the determination of rate data. Useful information may also be obtainable from the shape of the lines recorded on recorder 5 and/or by measurement of the torque on the rotors 11 and 12. The apparatus may also be capable of being used in mechanistic studies of the oxidation of polymers.

The size of the sample used in the process of the present invention depends primarily on the size of cavity 10 but the sample may be for example 20–50 cm$^3$. Such samples are capable of being used, after completion of a determination of oxidative stability, for the preparation of test samples on which physical properties or the like may be determined. Thus correlations of oxidation and other properties of the polymer may be made. The present invention, therefore, is capable of producing samples of oxidized polymer of essentially homogeneous composition in a size that allows additional tests to be conducted. Such a capability is important as all additives of a particular class, e.g., antioxidants may not function in the same manner and may have different effects on the properties of a polymer at the same degree of oxidation.

The present invention is illustrated by the following examples.

EXAMPLE I

In this example and the examples hereinafter the apparatus used was essentially the apparatus described hereinbefore. Cavity 10 had a volume of approximately 70 cm$^3$ and elongated vent pipe 23 had an L/D of approximately 880. The total volume of the apparatus was approximately 170 cm$^3$. The temperature, oxygen partial pressure and torque measuring means were calibrated prior to use. The oxygen measuring means was a Beckman Instruments, Inc. Model 777 oxygen analyzer and the pump used was a peristaltic pump. The desired temperature was obtained by electrical heating means.

The temperature as measured by thermocouple 13 was adjusted to that required for the experiment. A weighed sample of polymer was fed to cavity 10 through the orifice formed by removal of removable plug 17. Plug 17 was then replaced and clamped into position. The system was then evacuated to a pressure of less than 10 mm Hg and then nitrogen was admitted to the system. After four minutes the nitrogen was evacuated from the system and replaced with air. The peristaltic pump was then started and vent 30 was opened. The rotors were rotated at 50 rpm.

After the experiment was completed the apparatus was disassembled and the polymer sample was removed.

The induction period for the oxidation of an ethylene/butene-1 copolymer having a density of 0.924 and a melt index (measured by the method of ASTM D-1238, Condition E) of 5 was measured at various temperatures on approximately 38 gm samples of polymer. The polymer contained no additives, i.e., it was an unstabilized polymer. From the results obtained the energy of activation for the induction period was calculated.

The results were as follows:

| Polymer Temperature (° C) | Induction Period (minutes) |
|---|---|
| 150 | 28 |
| 160 | 12 |
| 170 | 6.5 |
| 180 | 4.2 |
| 190 | 2.9 |

The energy of activation (Ea) was calculated to be 22 k calories/mole.

EXAMPLE II

The procedure of Example I was repeated except that the polymer contained 0.04% of IRGANOX 1010 antioxidant (tetrakis[methylene 3-(3',5'-di-tert-butyl-4" hydroxyphenol)propinoate]methane).

The results were as follows:

| Polymer Temperature (° C) | Induction Period (minutes) |
|---|---|
| 205 | 42 |
| 210 | 23 |
| 215 | 12 |
| 220 | 7.5 |

The energy of activation (Ea) was calculated to be 50 k calories/mole.

EXAMPLE III

To show the effect of the type of antioxidant on the induction period of a polymer, the polymer of Example I was melt blended with a series of phenolic antioxidants under an atmosphere of nitrogen at 160° C. The amount of antioxidant was adjusted so that the same concentration of phenolic groups was present in the polymer.

The induction period was measured at 200° C. Further details and the results obtained were as follows:

| Antioxidant* | Concentration of Antioxidant (weight %) | Induction Period (minutes) |
|---|---|---|
| A | 0.032 | 13.6 |
| B | 0.026 | 19.3 |
| C | 0.018 | 48.6 |

*A = 1,6 hexamethylene bis(3,5-di-tert-butyl-4-hydroxy-hydro-cinnamate)
B = 1,3,5-trimethyl-2-4-6-tris(3,5-di-tert-butyl-4-hydroxy-benzyl)benzene
C = 4,4'-thiobis(6-tert-butyl-m-cresol)

EXAMPLE IV

The procedure of Example I was repeated using a sample of a stabilized polyester elastomer (HYTREL 4056). The oxidative stability of the sample was measured at 180° C., 200° C. and 220° C.

No induction period was observed at any of the above temperatures.

The initial oxidation rate increased with increasing temperature, being 2.4 times higher at 200° C. and 3.2 times higher at 220° C. than at 180° C.

EXAMPLE V

The procedure of Example I was repeated using a variety of polymers. In some cases the rotation of the rotors was not 50 rpm. Details of the experiments and the results obtained are as follows:

| Polymer** | Temperature (° C) | Rotation of Rotors (rpm) | Induction Period (minutes) | Maximum Rate of Oxidation**** (observed) |
|---|---|---|---|---|
| A | 220 | 50 | none*** | |
| B | 210 | 50 | 31 | 4.2 |
| C | 170 | 22–38 | none | 17 |
| D | 170 | 50 | 25 | 8.3 |
| E | 170 | 25 | none | 2.2 |
| F | 220 | 22 | 3.8 | 17 |
| G | 190 | 50 | 88 | 4.5 |
| H | 170 | 30 | none | 0.4 |

**A = PROFAX 6301 unstabilized polypropylene
B = WITRON 131 polybutylene
C = KRATON 1101 styrene-butadiene-styrene block copolymer
D = VISTALON MD 702 ethylene-propylene copolymer
E = NORDEL 1500 ethylene-propylene-hexadiene copolymer
F = KDRATON GX 6500 styrene-ethylene-butylene-styrene block copolymer
G = ELVAX 360 ethylne-vinyl acetate copolymer
H = ROYALENE 1M 7200 ethylene-propylene-ethylidene-norbornene copolymer.
***none = no induction period observed.
****in mm of Hg. min $^{-1}$ g $^{-1}$.

The embodiments of the invention in which an exclusive property or privilege is claimed are defined as follows:

1. Apparatus for the determination of the oxidative stability of polymers exhibiting viscous or visco-elastic flow at the temperature of said determination, said apparatus comprising
   (a) a mixing head having a cavity adapted to receive thermoplastic polymer and to be sealed;
   (b) means located within said cavity capable of subjecting polymer to shear;
   (c) heating means adapted to control the temperature of polymer in said mixing head;
   (d) analyzing means capable of measuring the oxygen content of a gas;
   (e) circulating means adapted to circulate gas from within the mixing head through the analyzing means and back to the mixing head;
   (f) pressure control means adapted to control the pressure of gas at atmospheric pressure, said pressure control means inhibiting extraneous dilution; and
   (g) means adapted to replace a first gas with a second gas.

2. The apparatus of claim 1 in which the means to heat the polymer are electrical means.

3. The apparatus of claim 2 in which the means to control the pressure is an elongated tube having at one end thereof a vessel equipped with a small opening connecting with the atmosphere, said vessel being adapted to be flushed with inert gas, the other end of said elongated tube being connected to the means to circulate the gas.

4. The apparatus of claim 3 in which the elongated tube has a ratio of length to diameter of at least 800.

5. The apparatus of claim 1 in which the pump is a peristaltic pump.

6. The apparatus of claim 1 in which the volume of the cavity is in the range of about 20–100 cm$^3$.

7. The apparatus of claim 1 in which the volume of the cavity is in the range of about 30–70 cm$^3$.

8. A method for determining the oxidative stability of polymers under shear conditions, said method comprising the steps of:
  (a) heating polymer to a pre-selected temperature in the presence of a first gas that is inert with respect to the polymer, said polymer being viscous or visco-elastic at the pre-selected temperature,
  (b) replacing the inert gas with an oxygen-containing gas, said oxygen-containing gas being at atmospheric pressure, and
  (c) while subjecting the polymer to shear measuring the amount of oxygen in the oxygen-containing gas over a period of time, the pressure of the oxygen-containing gas being maintained at atmospheric pressure by addition of a second gas that is inert with respect to the polymer.

9. The method of claim 8 in which the polymer is viscous at the pre-selected temperature.

10. The method of claim 8 in which the polymer is visco-elastic at the pre-selected temperature.

11. The process of claim 8 in which 20–50 cm$^3$ of polymer are heated in step (a).

12. The method of claim 8 in which the amount of oxygen in the oxygen-containing gas is measured by passing said gas from the polymer through an oxygen analyzer and back to the polymer.

13. The method of claim 12 in which the first gas and the second gas are nitrogen.

14. The method of claim 13 in which the oxygen-containing gas is air.

15. The method of claim 14 in which the polymer is a thermoplastic polymer.

16. The method of claim 14 in which the polymer is an elastomeric polymer.

17. The method of claim 14 in which the polymer is a poly-α-olefin.

18. The method of claim 14 in which the polymer is selected from homopolymers of ethylene and copolymers of ethylene and higher α-olefins.

* * * * *

UNITED STATES PATENT OFFICE
CERTIFICATE OF CORRECTION

PATENT NO. : 4,120,660
DATED : October 17, 1978
INVENTOR(S) : Joseph Donnelly Trizisky It is certified that error appears in the above-identified patent and that said Letters Patent are hereby corrected as shown below:

Change name of assignee to -- Du Pont of Canada, Limited --.

Signed and Sealed this

Twenty-seventh Day of February 1979

[SEAL]

Attest:

RUTH C. MASON
Attesting Officer

DONALD W. BANNER
Commissioner of Patents and Trademarks